United States Patent [19]

Takeuchi et al.

[11] Patent Number: 5,304,483

[45] Date of Patent: Apr. 19, 1994

[54] CONTROLLING CULTIVATION CONDITIONS FOR ANIMAL CELLS

[75] Inventors: Kouji Takeuchi, Nagareyama; Hideo Kawaguchi, Hachioji; Tadashi Ishibashi, Kodaira; Norio Shimizu, Kokubunji, all of Japan

[73] Assignee: Hitachi, Ltd., Tokyo, Japan

[21] Appl. No.: 493,369

[22] Filed: Mar. 14, 1990

[30] Foreign Application Priority Data

Mar. 14, 1989 [JP] Japan .................................. 1-59721
Jul. 14, 1989 [JP] Japan .................................. 1-180196

[51] Int. Cl.$^5$ .......................... C12N 5/00; C12N 5/02; C12N 5/06
[52] U.S. Cl. .............................. 435/240.25; 435/240.1; 435/240.2
[58] Field of Search ........... 435/240.2, 240.23, 240.24, 435/240.243, 240.25

[56] References Cited

FOREIGN PATENT DOCUMENTS

| | | |
|---|---|---|
| 2578266 | 9/1986 | France . |
| 6136915 | 5/1984 | Japan . |
| 61-257181 | 11/1986 | Japan . |
| 63-233780 | 1/1989 | Japan . |
| 8801643 | 3/1988 | PCT Int'l Appl. ............... 435/240.2 |
| 1090758 | 11/1967 | United Kingdom . |

OTHER PUBLICATIONS

Biotechnology And Bioengineering, vol. 27, No. 6, Jun., 1985, pp. 837–841. "Application of L-(+)-lactate electrode for clinical analysis and monitoring of tissue culture medium".
Journal Of Fermentation Technology, vol. 65, No. 3, 1987, "Effects of Lactate and Ammonium on the Oxygen Uptake Rate of Human Cells", T. Kimura et al, pp. 341–344.
Japan Journal Experimental Medicine, vol. 28, No. 2, 1958, "Establishment of Cell Strains of Rat Ascites Hepatoma Cells in Tissue Culture", T. Takaoka et al, pp. 115–127.
"Observations on the Carbohydrate Metabolism of Tumours", H. Crabtree, Laboratory Of The Imperial Cancer Research Fund, London, England, 1929.
Kagaku Kogaku Ronbunshu, 14, (3), 1988, M. Tokashiki et al, pp. 337–341.
Biotechnology And Bioengineering, vol. XXIII, "Development of a Hollow-Fiber System for Large-Scale Culture of Mammalian Cells", pp. 79–95; 1981.
Thomas "Nutrients, Oxygen, and pH" Chapter 5 in *Mammalian Cell Technology*, Thilly, (Editor), 1986, Butterworths Boston, London, Durban, Singapore, Sydney, Toronto, Wellington, pp. 109–130.
Paul "Carbohydrate And Energy Metabolism" Chapter 7 in *Cells And Tissues In Culture: Methods, Biology And Physiology*, vol. 1, Willmer, E. N. (Editor), 1965, Academic Press, London, New York pp. 239–276.
McKay, et al, Glucose Transport And Metabolism In Cultured Human Skin Fibroblasts Biochemica et Biophyska Acta vol. 762 pp. 198–204 1983.
Lehninger Biochemistry 2nd Edition pp. 244≧245, 849 Worth Publishers, Inc. New York, N.Y. 1975.

*Primary Examiner*—George C. Elliott
*Attorney, Agent, or Firm*—Fay, Sharpe, Beall, Fagan, Minnich & McKee

[57] ABSTRACT

Stable, long-term cultures of animal cells are accomplished by calculating the ratio of lactic acid formed by the cells to the glucose consumed by the cells (the L/G ratio) and controlling the cultivation conditions to maintain the L/G ratio between the limits of from greater than 0 to 0.6. When the ratio is outside the desired range, the dissolved oxygen concentration in the medium is increased and/or the glucose concentration in the medium is decreased.

11 Claims, 7 Drawing Sheets

CONTROLLING CULTIVATION CONDITIONS FOR ANIMAL CELLS

BACKGROUND OF THE INVENTION

This invention relates to a process for controlling cultivation conditions.

Animal cells can produce proteins which cannot be produced by recombinant microorganisms, for example, those to which oligosaccharides are bound, those having high molecular weights and those having complicated stereochemical structures. Therefore, it has attracted public attention to produce these proteins by culturing animal cells. In particular, there has been an urgent demand to establish a process for the mass production of animal cells.

SUMMARY

Conventional microorganism culture systems can hardly be applied to the mass production of animal cells for the following reason. An animal cell has no cell wall and thus shows a poor resistance against shearing forces caused by stirring. Serum contained in a culture medium would be foamed during aeration. The long generation time of animal cells requires maintaining the system axenic for several tens of hours. It is particularly required to maintain a sensor for measuring the dissolved oxygen concentration in the culture medium stable for a long time, since the cultivation should be continued for a long time. However, an oxygen sensor would be damaged by heat or a change in pressure during steam sterilization. Further, the prolonged use of an oxygen sensor would sometimes cause the drying up of liquid in the sensor or the formation of a protein membrane at the sensor/liquid interface, which make the measurement impossible. When these troubles make the measurement of the dissolved oxygen concentration impossible, the controlled cultivation cannot be continued any more. The excessive supply of oxygen would make the animal cells toxic, while the shortage of oxygen would lower the proliferation.

In addition, there are no known optimum cultivation conditions for animal cells.

The failure in the measurement of the dissolved oxygen concentration and the lack of any procedure for determining the growth activity of animal cells makes it difficult to continue the cultivation for a prolonged period of time.

Accordingly, it is an object of the present invention to stably culture animal cells for a long time.

The above mentioned object can be achieved by calculating the ratio of lactic acid formed by the cultivation of animal cells to glucose consumed thereby, determining the growth conditions of the animal cells therefrom and thus controlling the cultivation conditions.

Accordingly, the present invention provides a process for controlling cultivation conditions for animal cells characterized by measuring the glucose concentration and lactic acid concentration in a culture medium of animal cells and, when the ratio of the formed lactic acid to the consumed glucose (L/G) obtained from the resulting data is outside a fixed range, controlling the dissolved oxygen concentration and/or glucose concentration in the culture medium depending thereon. The above mentioned fixed range may be preferably from greater than 0 to 0.6. When the ratio is outside the range, the dissolved oxygen concentration and/or glucose concentration in the culture medium may be controlled by increasing the dissolved oxygen concentration in the culture medium and/or decreasing the glucose concentration therein. Also, the device may be provided with sensors for measuring the glucose concentration and lactic acid concentration in the culture medium, a control for calculating the ratio of the formed lactic acid to the consumed glucose based on the resulting data and comparing the ratio thus calculated with the fixed range which has been preliminarily input, and a control for controlling the dissolved oxygen concentration and/or glucose concentration in the culture medium based on the result of the comparison.

The cultivation process of the present invention may be applied to any animal cells that can express a gene of an enzyme which assimilates lactic acid. An example of the enzyme assimilating lactic acid is cardiac type lactate dehydrogenase. An example of the animal cells is rat ascites hepatoma cell JTC-1 strain which originates from liver.

The JTC-1 strain, which is described in Journal of Experimental Medicine, 28 (2), 115–117 (1958) and has been authorized by Japan Society of Tissue Culture, can be readily obtained.

Furthermore, the present invention provides a cultivation process for animal cells wherein the control of cultivation conditions is conducted and a cultivation device for animal cells provided with the device for controlling cultivation conditions.

BRIEF DESCRIPTION OF THE DRAWINGS

Further objects, features and advantages of the present invention will become more clear from the following detailed description of a preferred embodiment, shown in the drawing, wherein.

DETAILED DESCRIPTION OF THE PREFERRED EMBODIMENT

Under aerobic conditions, animal cells acquire energy by converting glucose into carbon dioxide and water via the tricarboxylic acid cycle. The use of the tricarboxylic acid cycle is suitable for the growth of animal cells, and 38 mol of adenosine triphosphate (ATP) is formed from 1 mol of glucose in this cycle. Under conditions where oxygen is insufficient, on the other hand, animal cells acquire energy by converting glucose into lactic acid via the glycolysis pathway depending on the Pasteur effect. In this later case, only two mol of ATP can be formed from one mol of glucose. Thus the exclusive use of the glycolysis pathway results in an extremely low efficiency of the utilization of glucose. The conditions of the supply of oxygen and the growth activity of the cells is determined by using the ratio of the formed lactic acid to the consumed glucose as an indication.

Even though a sufficient amount of oxygen is supplied, furthermore, lactic acid would be formed by Crabtree's effect when a culture medium contains glucose at a high concentration [cf. Crabtree, Biochemistry, 23, 537–545 (1929)]. In this case, the cells acquire energy by using the glycolysis pathway exclusively. Thus the growth activity of the cells is low.

The growth activity of cells is determined by measuring the glucose concentration and lactic acid concentration in a culture medium and using a ratio of the formed lactic acid to the consumed glucose (L/G) obtained from the data as an indication to thereby grasp the cultivation conditions and control the same.

The preferred range of the L/G ratio, has been established through the following cultivation experiments conducted under various conditions, and is found to be from greater than 0 to 0.6.

Figure 1A:
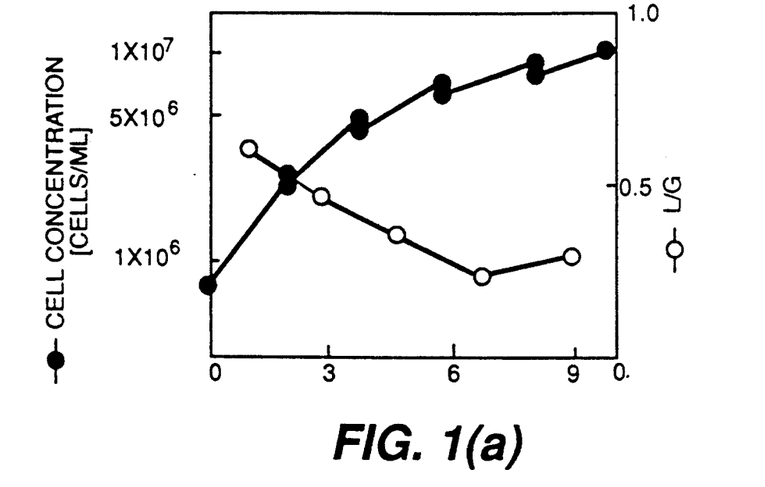
FIGS. 1(a) and 1(b), 2(a) and 2(b), 3(a) and 3(b), 4(a) and 4(b) and 5(a) and 5(b) show the results of the Experimental Examples.
Figure 1B:
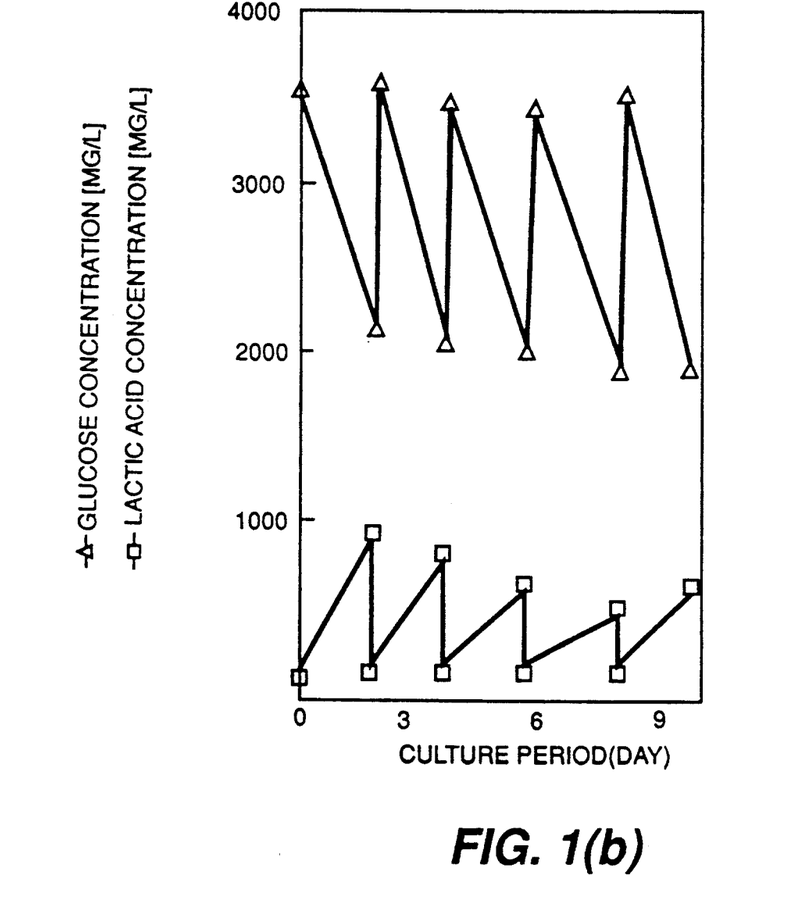

An air filter (mfd. by Gelman Science, 7.5 cm$^2$) was attached to the lid of a 200-ml tapping culture flask in such a manner that an oxygen-containing gas stream was introduced therethrough into the container. 80 ml of a DM160-AU medium (mfd. by Kyokuto Seiyaku Kogyo K. K.) containing 10% of new born bovine serum was fed into the container and then inoculated with seed cells, JTC-1 strain (rat abdominal hepatoma cells) at a concentration of $1 \times 10^6$ cells/ml. Then the cells were cultured under conditions of stirring at 400 rpm, 37° C. and a $CO_2$ incubator. The culture medium was centrifuged at 1200 rpm for 10 minutes every two days and the centrifugally separated cells were placed in a new medium, i.e., exchange the whole medium. The initial glucose concentration of the culture medium was adjusted to 3500 ppm at the time of each exchange. Before and after each exchange of the whole medium, 2-ml portions of the culture medium were sampled and the glucose concentration and lactic acid concentration of each sample was measured with an enzyme sensor. Further the cell concentration was measured with a hemacytometer. FIG. 1 shows the results. The cells grew well and the cell concentration reached $1 \times 10^7$ cells/ml on the tenth day. The L/G was as high as 0.5 at the early part of the cultivation, then slowly decreased and finally reached 0.3. Thus it was found that an L/G of 0.6 or below indicated that the cultivation conditions were aerobic and a sufficient amount of glucose was supplied, i.e., the cells showed a high growth activity and the optimum cultivation conditions were established. In the following examples, conditions are the same except where differences are noted.

Figure 2A:
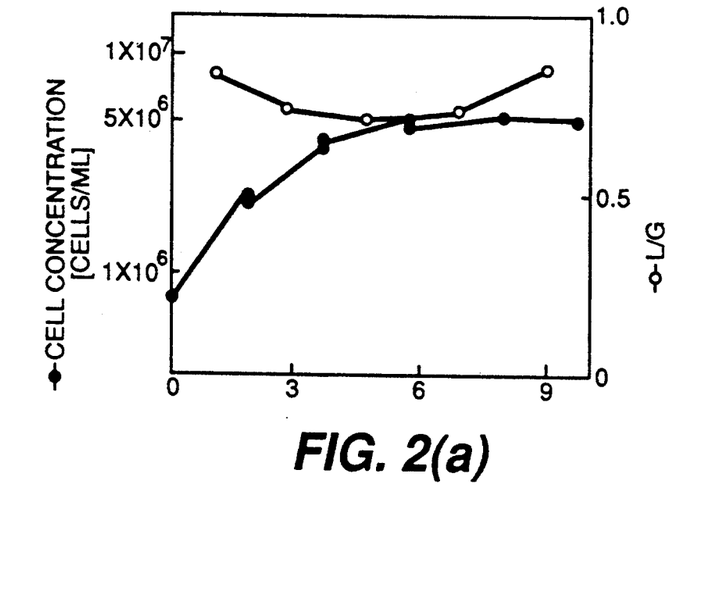
Figure 2B:
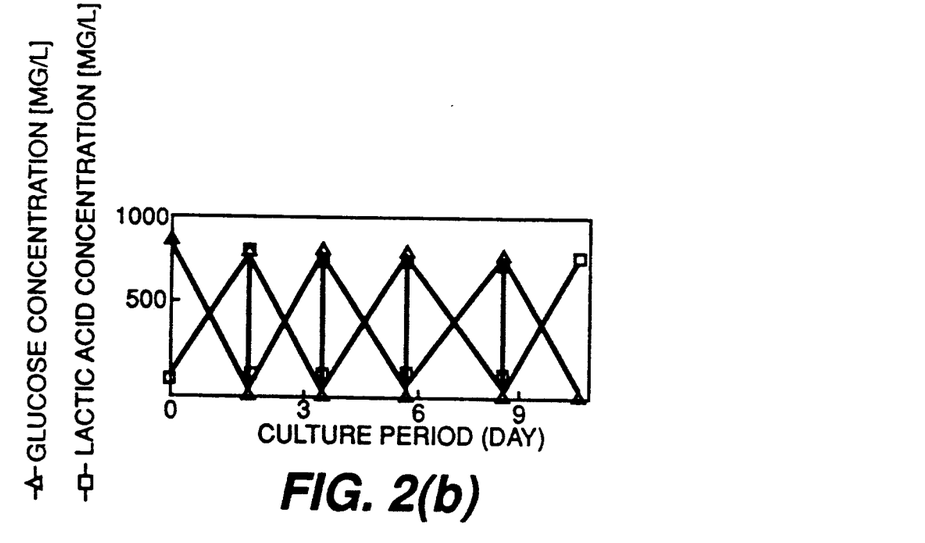

Next, the glucose concentration in the culture medium at the time of each exchange of the whole medium was adjusted to 1000 ppm and the air filter was removed. Namely, the cultivation was carried out under hermetically sealed conditions. FIG. 2 shows the results. The final cell concentration was $5.5 \times 10^6$ cells/ml while the L/G exceeded 0.6 throughout most of the cultivation period. Thus it was found that the growth activity of the cells was lowered when the L/G exceeded 0.6 and the glucose concentration was not excessively high.

Figure 3A:
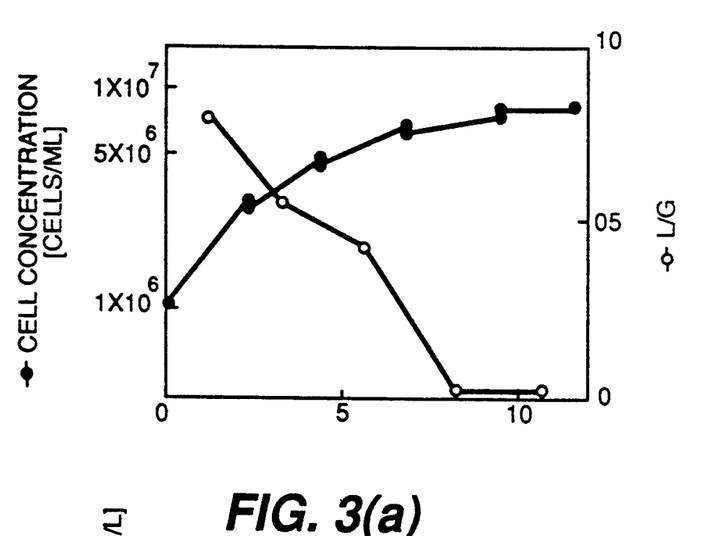
Figure 3B:
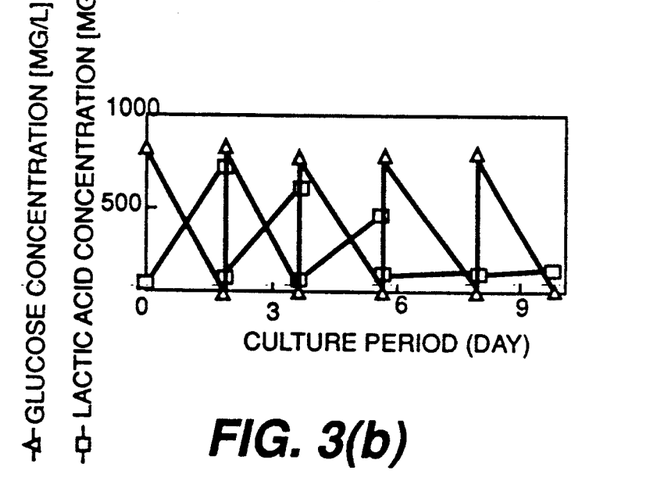

Next, the glucose concentration in the culture medium at the time of each exchange of the whole medium was adjusted to 1000 ppm and the air filter was attached to the lid. FIG. 3 shows the results. The final cell concentration was $7.5 \times 10^6$ cells/ml while the L/G decreased with the lapse of time and reached O on the eighth day simultaneously with the consumption of the glucose. Thus it was found that the glucose concentration of 1000 ppm was insufficient for achieving a high-density cell concentration of $1 \times 10^7$ cells/ml or above.

Figure 4A:
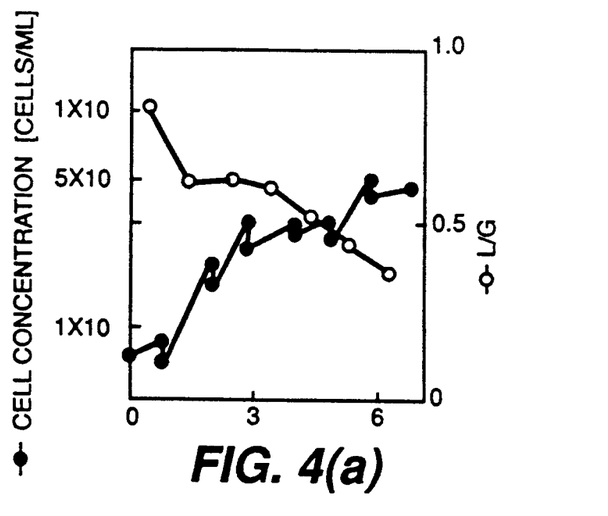
Figure 4B:
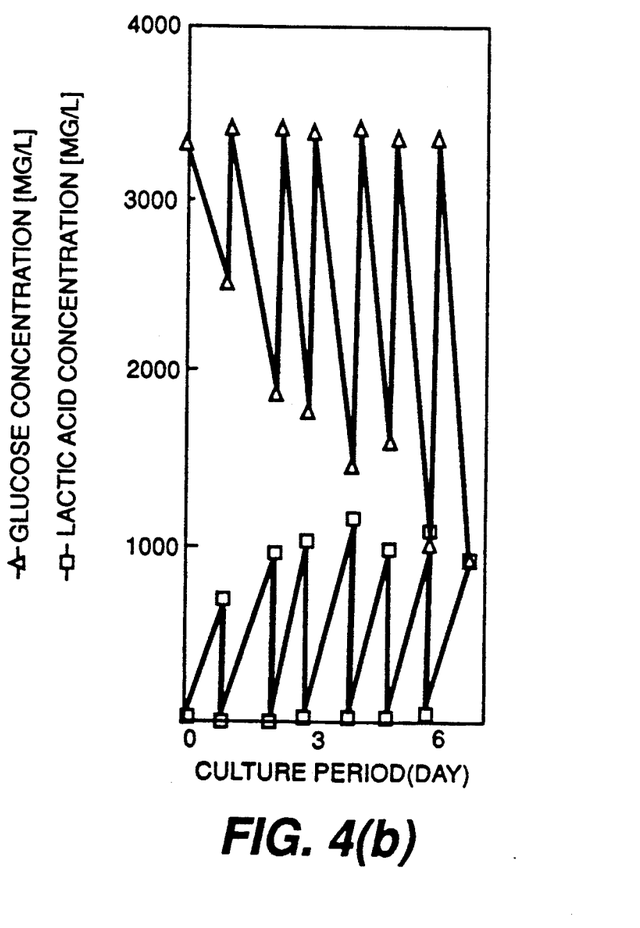

Then mouse hybridoma 11D-11-1 strain (parent strain: P3-U1) was cultured. An air filter was attached to the same tapping culture flask as the one described above to thereby introduce an oxygen-containing gas stream with variable oxygen concentrations into the container. 80 ml of a serum-free medium E-RDF+RD-1 (mfd. by Kyokuto Seiyaku Kogyo K. K.) was fed into the container and inoculated with seed cells 11D-11-1 at a concentration of $1 \times 10^6$ cells/ml. Then the cells were cultured under conditions of stirring at 300 rpm, 37° C. plus a $CO_2$ incubator. The culture medium was centrifuged at 1200 rpm for 10 minutes everyday to thereby exchange the whole medium. The initial glucose concentration of the culture medium was adjusted to 3423 ppm at the time of each exchange. Before and after each exchange of the whole medium, 2-ml portions of the culture medium were sampled and the glucose concentration and lactic acid concentration of each sample was measured with an enzyme sensor. Further the cell concentration was measured with a hemacytometer. FIG. 4 shows the results. On the fourth day of the cultivation, the cell concentration reached $3 \times 10^6$ cells/ml and the growth ceased, when the L/G exceeded 0.6. When the oxygen concentration of the oxygen-containing gas was adjusted to 60%, however, the cell concentration reached $5 \times 10^6$ cells/ml and the L/G decreased to 0.4 on the seventh day. Thus it was found that an L/G of 0.6 or below indicated that the cultivation was conducted under aerobic conditions and the cells showed a high growth activity, namely, conditions suitable for the growth were established.

Figure 5A:
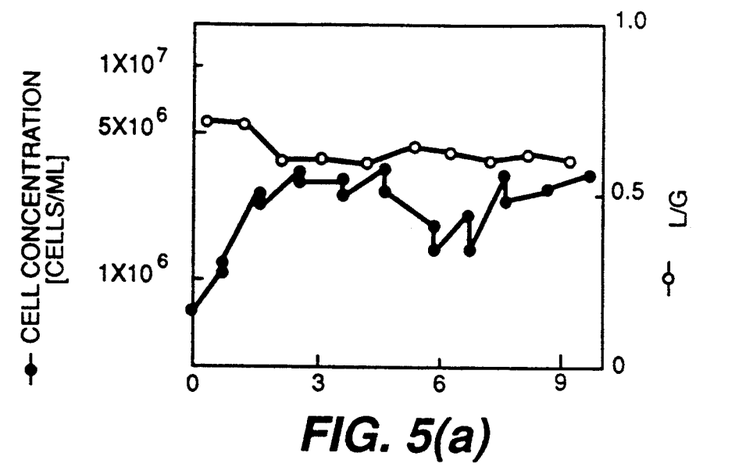
Figure 5B:
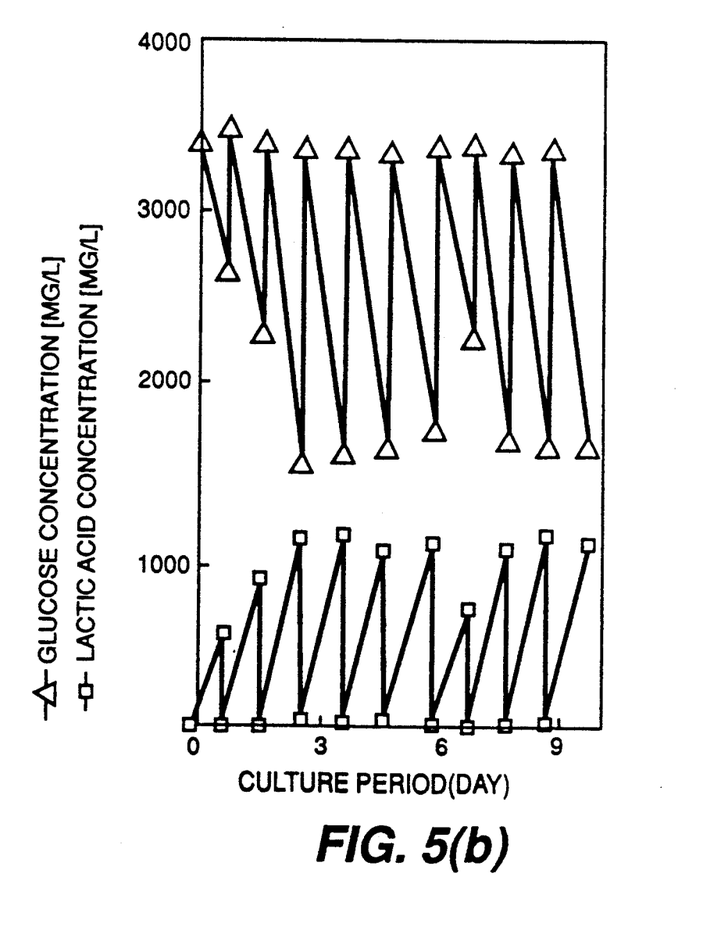

Next, the oxygen concentration of the oxygen containing gas was constantly kept at 20% and the cultivation was conducted. FIG. 5 shows the results. The cell concentration reached $3 \times 10^6$ cells/ml on the third day but the cells did not grow any more. The L/G exceeded 0.6 throughout the cultivation period. Thus it was found that the supply of oxygen was insufficient and the growth activity of the cells was lowered when the L/G exceeded 0.6 and the glucose concentration was not excessively high.

The results of these Experimental Examples show that the growth conditions of cells can be determined from the consumed glucose and the formed lactic acid, particularly their ratio. The cells particularly grew well when the L/G ranged from greater than O to 0.6, which suggests that the supply of glucose and oxygen under such conditions might be suitable for the growth of the cells.

In the process for controlling cultivation conditions according to the present invention, therefore, the dissolved oxygen concentration and/or glucose concentration in the culture medium should be controlled when the L/G is outside a fixed range, which preferably is from greater than 0 to 0.6.

The control may be conducted by increasing the dissolved oxygen concentration of the culture medium and/or decreasing the glucose concentration thereof. When the L/G exceeds 0.6, for example, the supply of oxygen is first increased and it is examined whether the L/G is lowered to 0.6. When the L/G is still above 0.6, the control can be achieved by decreasing the supply of glucose.

Figure 6:
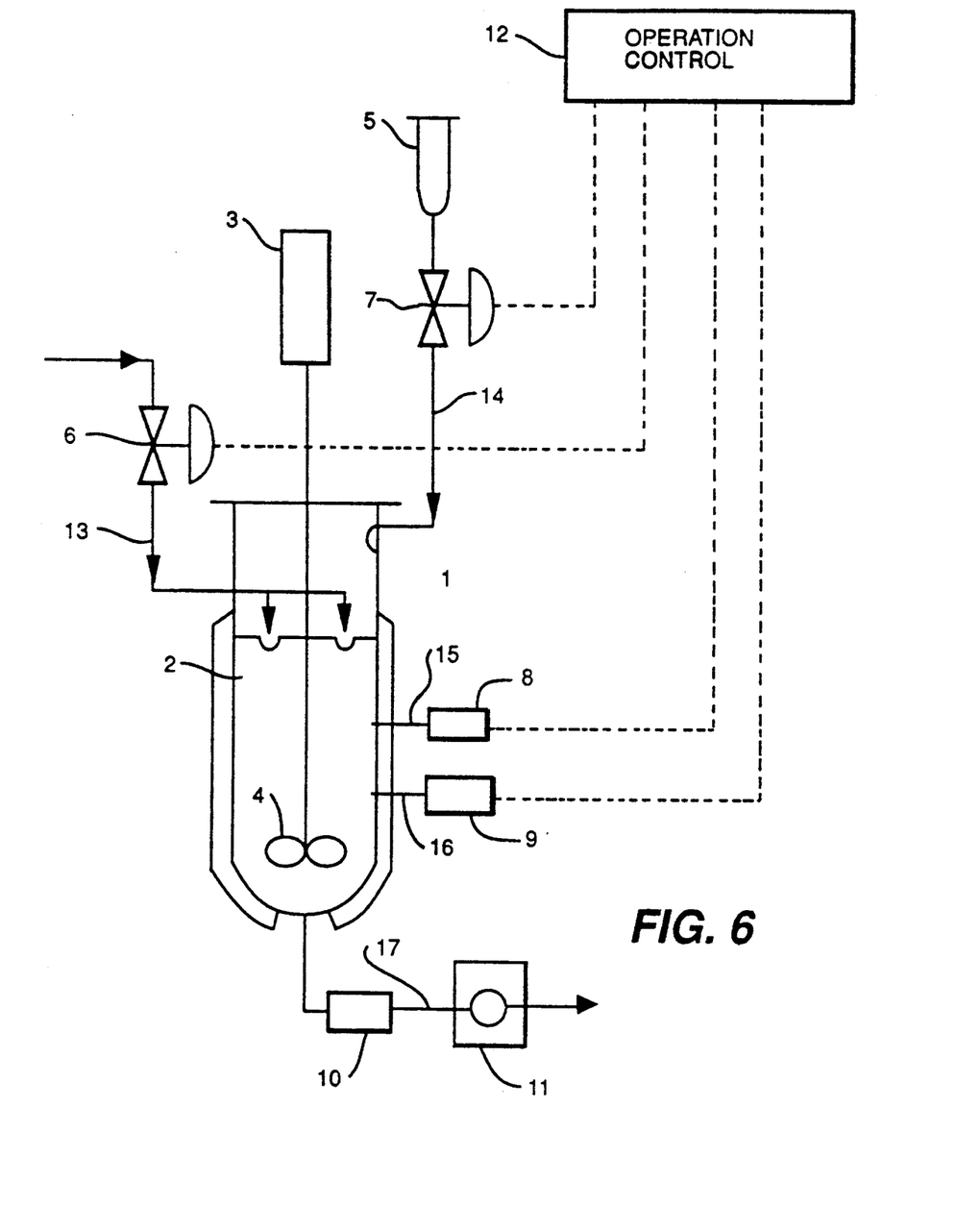
FIG. 6 is a schematic view of the cultivation device of the present invention.

Now an example of a cultivation provided with the controlling according to the present invention will be described by reference to FIG. 6. A fermentor 1 contains a culture medium 2 in which cells may be optionally immobilized, for example, on a microcarrier. The cells are suspended in the medium 2 by rotating stirring blades 4 with the use of a motor 3. Oxygen may be supplied by either overlay aeration, bubbling or membrane aeration. The oxygen-containing gas is fed into the fermentor 1 through a conduit 13 and the flow rate is controlled with a flow rate control valve 6. A reserve medium 2 containing glucose or an aqueous solution of glucose is in a tank 5. The glucose-containing solution is fed to the fermentor 1 through a conduit 14 and the flow rate thereof is controlled with a flow rate control valve 7. The cultivation may be conducted by, for example, semibatch culture or continuous culture. Continuous culture is suitable for mass production. The culture supernatant is separated from the cells by a cell/culture medium separator 10 and discharged out of the fermentor through a conduit 17 with the use of a culture supernatant pump 11. The concentrations of lactic acid and glucose in the culture medium 2 may be measured by, for example, using an enzyme sensor or liquid chromatography. Thus they are measured with a glucose concentration sensor 8 and a lactic acid concentration sensor 9 respectively. The data from sensors 8, 9 are input to an operation control 12 where calculations are performed and control signals generated according to the ratio L/G. Then the control signals are output toward the flow rate control valves 6 and 7 to control the supply of oxygen and the glucose, respectively.

The present inventors found that the ratio of the concentration of lactic acid formed in the culture medium to that of the consumed glucose (L/G) correlates to the dissolved oxygen concentration in the culture medium and to the growth conditions of the cells. They further found that the cells grew well when the L/G was within a fixed range, in particular, from greater than 0 to 0.6. Accordingly, cultivation conditions for animal cells may be appropriately controlled by maintaining the L/G within the range. In the present invention, the L/G is maintained within the range by controlling the dissolved oxygen concentration and/or glucose concentration.

To further illustrate the present invention, and not by way of limitation, the following example will be given.

EXAMPLE 1

Figure 7A:
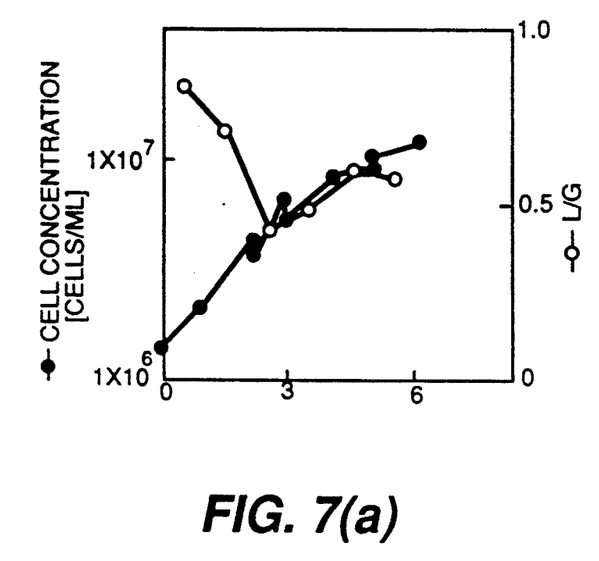
FIGS. 7(a) and 7(b) shows the results of an example of the embodiment of the present invention.
Figure 7B:
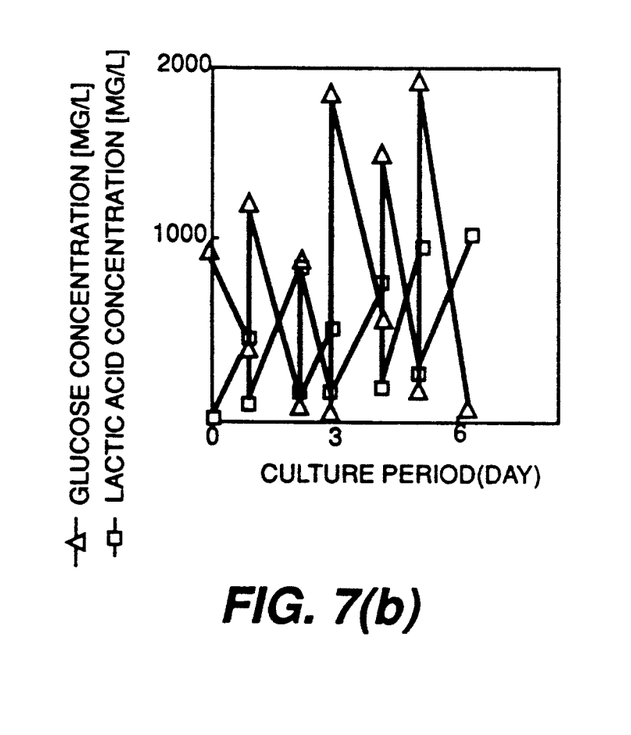

An air filter (mfd. by Gelman Science, 7.5 cm$^2$) was attached to the lid of a 200-ml tapping culture flask in such a manner that an oxygen-containing gas stream was introduced through the filter into the container. 80 ml of a DM160-AU medium (mfd. by Kyokuto Seiyaku Kogyo K. K.) containing 10% of new born bovine serum was fed into the container and then inoculated with seed cells JTC-1 strain (rat abdominal hepatoma cells) at a concentration of $1 \times 10^6$ cells/ml. Then the cells were cultured under conditions of stirring at 400 rpm, at 37° C., and a $CO_2$ incubator. The culture medium was centrifuged at 1200 rpm for 10 minutes everyday to thereby exchange the whole medium. Before and after each exchange of the whole medium, 2-ml portions of the culture medium were sampled, and the glucose concentration and lactic acid concentration of each sample was measured with an enzyme sensor. Further the cell concentration was measured with a hemacytometer. The glucose concentration of the medium to be exchanged was determined according to an assumed glucose consumption rate of the JTC strain of $1 \times 10^{-7}$ mg/cell/day. When the L/G exceeded 0.6, this value was decreased. When the L/G fell down to 0.4 or below, on the other hand, this value was increased for safety. FIG. 7 shows the results of the cultivation. The cell concentration reached $1 \times 10^7$ cells/ml on the fifth day. The L/G was high on the first day, slowly decreased thereafter and reached 0.4 on the third day. Then the supply of glucose was increased, which caused an increase in the L/G. Except for the first day, the L/G was within a range of from 0 to 0.6 and the cells grew well. Thus a high density cultivation of $1 \times 10^7$ cells/ml was effected.

The present invention makes it possible to stably control cultivation conditions for animal cells for a prolonged period of time.

While a preferred embodiment has been set forth along with modifications and variations to show specific advantageous details of the present invention, further embodiments, modifications and variations are contemplated within the broader aspects of the present invention, all as set forth by the spirit and scope of the following claims.

We claim:

1. A process for controlling culture conditions for animal cells in a culture medium containing glucose, comprising:

measuring the lactic acid concentration in the culture medium of animal cells;

measuring the glucose concentration in the culture medium; and controlling at least one of the dissolved oxygen concentration and glucose concentration in the culture medium when the ratio of the formed lactic acid to the consumed glucose (L/G) obtained from said steps of measuring is outside a fixed range from greater than 0 to 0.6 to return the ratio L/G to the fixed range.

2. A process for controlling cultivation conditions for animal cells as claimed in claim 1, wherein the controlling decreases the glucose concentration.

3. The method of claim 1 wherein the steps of measuring and controlling are conducted automatically.

4. The method according to claim 3, including stirring and adding oxygen to the medium substantially continuously for the entire method.

5. The method according to claim 4, including the step of periodically separating the animal cells from the medium and adding new medium to the separated cells a plurality of spaced apart times throughout the performance of the steps of measuring and controlling.

6. The method according to claim 2, including the step of periodically separating the animal cells from the medium and adding new medium to the separated cells a plurality of spaced apart times throughout the performance of the steps of measuring and controlling.

7. The method of claim 1, wherein the steps of measuring and controlling are conducted automatically.

8. The method according to claim 7, including stirring and adding oxygen to the medium substantially continuously for the entire method.

9. The method according to claim 3, including the step of periodically separating the animal cells from the medium and adding new medium to the separated cells a plurality of spaced apart times throughout the performance of the steps of measuring and controlling.

10. The method according to claim 7, including the step of periodically separating the animal cells from the medium and adding new medium to the separated cells a plurality of spaced apart times throughout the performance of the steps of measuring and controlling.

11. The method according to claim 1, including the step of periodically separating the animal cells from the medium and adding new medium to the separated cells a plurality of spaced apart times throughout the performance of the steps of measuring and controlling.

* * * * *